(12) United States Patent
Tsukamoto et al.

(10) Patent No.: US 10,512,768 B2
(45) Date of Patent: Dec. 24, 2019

(54) CLAMP DEVICE FOR FLEXIBLE TUBE

(71) Applicant: Nikkiso Company Limited, Tokyo (JP)

(72) Inventors: Daiki Tsukamoto, Shizuoka (JP); Ryo Kato, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 0 days.

(21) Appl. No.: 15/392,748

(22) Filed: Dec. 28, 2016

(65) Prior Publication Data

US 2017/0120038 A1 May 4, 2017

Related U.S. Application Data

(63) Continuation of application No. PCT/JP2015/067164, filed on Jun. 15, 2015.

(30) Foreign Application Priority Data

Jun. 30, 2014 (JP) .................................. 2014-134019

(51) Int. Cl.
  *F16K 7/06* (2006.01)
  *A61M 39/28* (2006.01)
  *A61M 1/14* (2006.01)

(52) U.S. Cl.
  CPC .............. *A61M 39/28* (2013.01); *A61M 1/14* (2013.01); *A61M 39/284* (2013.01); *F16K 7/066* (2013.01)

(58) Field of Classification Search
  CPC .. A61M 39/28; A61M 39/286; A61M 39/284; A61M 1/14; A61M 5/168;
  (Continued)

(56) References Cited

U.S. PATENT DOCUMENTS 350,850 A  10/1886 Tatum
3,419,245 A  12/1968 Scola
(Continued)

FOREIGN PATENT DOCUMENTS

EP  0637456 A1  2/1995
EP  2332611 A1  12/2009
(Continued)

OTHER PUBLICATIONS

International Search Report from the Japanese Patent Office for Application No. PCT/JP2015/067164, dated Jul. 14, 2015.
(Continued)

*Primary Examiner* — Craig J Price
*Assistant Examiner* — Andrew J Rost
(74) *Attorney, Agent, or Firm* — Young Basile Hanlon & MacFarlane, P.C.

(57) ABSTRACT

A clamp device for a flexible tube which can minimize the sealing area and prevent leakage of fluid and achieve easy release of the clamp device of a flexible tube. A clamp device for a flexible tube comprising: one branch formed with a first projection; the other branch formed with a second projection opposing to the first projection; an intermediate part connecting the one branch and the other branch each other; and an engaging part formed on a tip end of the other branch adapted to be engaged with an engaged part formed on a tip end of the one branch; flow of fluid within the flexible tube laid between the first projection and the second projection being able to be blocked by elastically bending the intermediate part and engaging the engaging part and the engaged part each other to clamp the flexible tube between the first and second projection wherein the clamp device comprises a positioning part for positioning the first and second projections in the longitudinal direction of the flex- (Continued)

ible tube under the clamped state of the flexible tube with engaging the engaging part and the engaged part each other.

19 Claims, 13 Drawing Sheets

(58) Field of Classification Search
CPC ... F16K 7/066; F16K 7/02; F16K 7/04; F16K 7/06; F16K 7/063; F16B 2/22; F16B 2/10
USPC ........................................ 251/10, 9; 604/250
See application file for complete search history.

(56) References Cited

U.S. PATENT DOCUMENTS

| | | | |
|---|---|---|---|
| 3,698,681 A | 10/1972 | Lacey | |
| 3,822,052 A | 7/1974 | Lange | |
| 4,053,135 A | 10/1977 | Saliaris | |
| 4,235,412 A | 11/1980 | Roth et al. | |
| 4,589,626 A | 5/1986 | Kurtz et al. | |
| 4,643,389 A | 2/1987 | Elson et al. | |
| 5,203,056 A | 4/1993 | Funk et al. | |
| 5,238,218 A | 8/1993 | Mackal | |
| 5,817,116 A * | 10/1998 | Takahashi | A61M 39/18 606/167 |
| 6,592,558 B2 | 7/2003 | Quah | |
| 6,698,681 B1 | 3/2004 | Guy et al. | |
| 8,262,639 B2 * | 9/2012 | Mathias | F16K 7/063 604/250 |
| 8,474,784 B2 | 7/2013 | Kashmirian et al. | |
| 10,322,278 B2 * | 6/2019 | Kato | A61M 39/284 |
| 10,384,049 B2 * | 8/2019 | Stanton | A61M 39/28 |
| 10,398,836 B2 * | 9/2019 | Kato | F16B 2/10 |
| 2004/0089828 A1 | 5/2004 | Werth | |
| 2006/0169934 A1 * | 8/2006 | Werth | A61M 39/284 251/9 |
| 2007/0261214 A1 | 11/2007 | Nerbonne | |
| 2010/0152681 A1 | 6/2010 | Mathias | |
| 2010/0268161 A1 | 10/2010 | Traversaz | |
| 2012/0232497 A1 | 9/2012 | Singh | |
| 2013/0310768 A1 * | 11/2013 | Ebara | A61M 5/168 604/250 |
| 2014/0074047 A1 * | 3/2014 | Calderon | A61M 39/28 604/250 |

FOREIGN PATENT DOCUMENTS

| | | |
|---|---|---|
| JP | S62-053667 A | 3/1987 |
| JP | H05-023792 B2 | 4/1993 |
| JP | 2001353215 A | 12/2001 |
| JP | 2003-235971 | 8/2003 |
| JP | 2005-027721 | 2/2005 |
| JP | 2009-022744 | 2/2009 |
| JP | 2012-075520 | 4/2012 |
| JP | 4922246 B2 | 4/2012 |
| WO | 2012/111310 A1 | 8/2012 |
| WO | 2014/162376 | 9/2014 |

OTHER PUBLICATIONS

Written Opinion from the Japanese Patent Office for Application No. PCT/JP2015/067164, dated Jul. 14, 2015.
International Search Report from the Japanese Patent Office for Application No. PCT/JP2016/053180, dated Apr. 26, 2016.
Potentially Related U.S. Appl. No. 15/665,635, filed Aug. 1, 2017.
Supplementary European Search Report, Application No. EP 15814858.5 dated Dec. 6, 2017.

* cited by examiner

CLAMP DEVICE FOR FLEXIBLE TUBE

FIELD

The present invention relates to a clamp device for clamping a flexible tube and blocking flow of fluid flowing therethrough at a clamped position by elastically bending an intermediate part of the clamp device and engaging one branch of the clamp device and an engaging part formed on the other branch of the clamp device each other to clamp the flexible tube laid between a first projection and a second projection of the clamp device.

BACKGROUND

In general, a blood circuit applied to a dialysis apparatus uses flexible tubes for passing blood of a patient therethrough, physiological saline or medicines to be dosed therethrough and connecting various medical instruments such as a dialyzer, chambers etc. A clamp device of the prior art generally comprises one branch formed with a first projection, the other branch formed with a second projection arranged oppositely to the first projection, an intermediate part connecting the one branch and the other branch each other, and an engaging part formed on the other branch of the clamp device adapted to engage the one branch of the clamp device as disclosed in Patent Document 1 below.

According to the clamp device of the prior art, it is possible to clamp the flexible tube and block flow of fluid flowing therethrough at the clamped position by elastically bending an intermediate part of the clamp device and engaging the one branch of the clamp device with the engaging part of the other branch of the clamp device to clamp the flexible tube laid between the first projection and the second projection of the clamp device. In addition, the clamp device of the prior art is provided with a guide part for guiding the one branch to the engaging part of the other branch to keep the clamping workability and prevent lateral displacement of the one branch of the clamp device during clamping work.

Patent Document 1: JP 2001-353215 A

However, although the clamp device of the prior art described above can prevent the lateral displacement of the one branch of the clamp device during clamping work, it does not have any effective mechanism for preventing the longitudinal displacement of the flexible tube during clamping work. Accordingly, it is afraid that the flexible tube would be clamped at a position in which the first projection and the second projection are longitudinally displaced when the first projection and the second projection are not exactly designed with respect to the longitudinal direction of the flexible tube and thus leakage of fluid would be caused. For surely performing the clamping of the flexible tube even at the longitudinally displaced position of the first and second projections, it is necessary to enlarge opposite areas ("sealing area") of the first and second projections. However, it is afraid the enlargement of sealing area would make the clamping force excessive and accordingly a large force would be required when releasing the clamp of the flexible tube by disengaging the one branch from the engaging part and this would worsen the workability.

It is, therefore, an object of the present invention to provide a clamp device for a flexible tube which can minimize the sealing area and also prevent leakage of fluid as well as achieve easy release of the clamp device of a flexible tube.

SUMMARY

For achieving the object of the present invention, there is provided according to the teachings herein a clamp device for a flexible tube comprising one branch formed with a first projection; the other branch formed with a second projection opposing to the first projection; an intermediate part connecting the one branch and the other branch each other; and an engaging part formed on the other branch adapted to be engaged with the one branch; flow of fluid within the flexible tube laid between the first projection and the second projection being able to be blocked by elastically bending the intermediate part and engaging the engaging part and the one branch each other to clamp the flexible tube between the first projection and the second projection characterized in that the clamp device further comprises a positioning part for performing a relative positioning of the first and second projections in the longitudinal direction of the flexible tube under the clamped state of the flexible tube with engaging the engaging part and the one branch each other.

According to the present teachings, there is provided a clamp device for a flexible tube of the teachings herein wherein said positioning part comprises a fitting part and a fitted part each formed on the one branch or the other branch, and wherein the relative positioning of the first projection and the second projection can be achieved by fitting the fitting part into the fitted part under a state in which the one branch is engaged by the engaging part of the other branch.

According to the teachings herein, there is provided a clamp device for a flexible tube of the teachings herein wherein said fitting part comprises a convex part and the fitted part comprises a concave part, and wherein the relative positioning of the first projection and the second projection can be achieved by fitting the convex part into the concave part under a state in which the one branch is engaged by the engaging part of the other branch.

According to the teachings herein, there is provided a clamp device for a flexible tube of the teachings herein wherein the clamp device further comprises wall parts extending substantially vertically from both side edges of the one branch or the other branch, and wherein the fitting part or the fitted part is formed on the wall parts.

According to the teachings herein, there is provided a clamp device for a flexible tube of the teachings herein wherein said wall parts extend substantially vertically from both side edges of the one branch or the other branch and enable the one branch to be guided during the one branch is engaged by the engaging part of the other branch.

According to the teachings herein, there is provided a clamp device for a flexible tube of the teachings herein wherein the clamp device further comprises separator parts projected from inner surfaces of the wall parts toward inside for separating the flexible tube laid between the first projection and the second projection away from the wall parts.

According to the teachings herein, there is provided a clamp device for a flexible tube of the teachings herein wherein said engaging part is formed on the tip end of the other branch and adapted to be engaged by an engaged part formed on the tip end of the one branch, and wherein the first projection, the second projection and the positioning part are formed at positions nearer to the intermediate part than the formed positions of the engaged part and the engaging part respectively of the one branch and the other branch.

According to the teachings herein, there is provided a medical instrument circuit to which the clamp device for a flexible tube of the teachings herein is attached.

According to the teachings herein, since the clamp device further comprises a positioning part for performing a relative positioning of the first and second projections in the longitudinal direction of the flexible tube under the clamped state of the flexible tube with engaging the engaging part and the one branch each other, it is possible to minimize the sealing area and also prevent leakage of fluid as well as achieve easy release of the clamp device of a flexible tube.

According to the teachings herein, since the positioning part comprises a fitting part and a fitted part each formed on the one branch or the other branch and the relative positioning of the first projection and the second projection can be achieved by fitting the fitting part into the fitted part under a state in which the one branch is engaged by the engaging part of the other branch, it is possible to more securely perform the relative positioning of the first and second projections in the longitudinal direction of the flexible tube.

According to the teachings herein, since the fitting part comprises a convex part and the fitted part comprises a concave part and the relative positioning of the first projection and the second projection can be achieved by fitting the convex part into the concave part under a state in which the one branch is engaged by the engaging part of the other branch, it is possible to more surely perform by a simple structure the relative positioning of the first and second projections in the longitudinal direction of the flexible tube.

According to the teachings herein, since the clamp device further comprises wall parts extending substantially vertically from both side edges of the one branch or the other branch, and wherein the fitting part or the fitted part is formed on the wall parts, it is possible to more smoothly and surely perform the fitting of the fitting part into the fitted part.

According to the teachings herein, since the wall parts extend substantially vertically from both side edges of the one branch or the other branch and enable the one branch to be guided during the one branch is engaged by the engaging part of the other branch, it is possible to perform the guidance of the one branch in addition to the relative positioning of the first and second projections in the longitudinal direction of the flexible tube.

According to the teachings herein, since the clamp device further comprises separator parts projected from inner surfaces of the wall parts toward inside for separating the flexible tube laid between the first projection and the second projection away from the wall parts, it is possible to perform the radial positioning of the flexible tube in addition to the relative positioning of the first and second projections in the longitudinal direction of the flexible tube.

According to the teachings herein, since the engaging part is formed on the tip end of the other branch and adapted to be engaged by an engaged part formed on the tip end of the one branch and the first projection, the second projection and the positioning part are formed at positions nearer to the intermediate part than the formed positions of the engaged part and the engaging part respectively of the one branch and the other branch, it is possible to perform the engagement of the engaging part and the engaged part with smaller force as well as to more securely perform the relative positioning of the first and second projections in the longitudinal direction of the flexible tube.

According to the teachings herein, it is possible to provide a medical instrument circuit having effects provided by the clamp device for a flexible tube of the teachings herein.

DETAILED DESCRIPTION

A first embodiment of the present invention will be hereinafter described with reference to the drawings.

Figure 1:
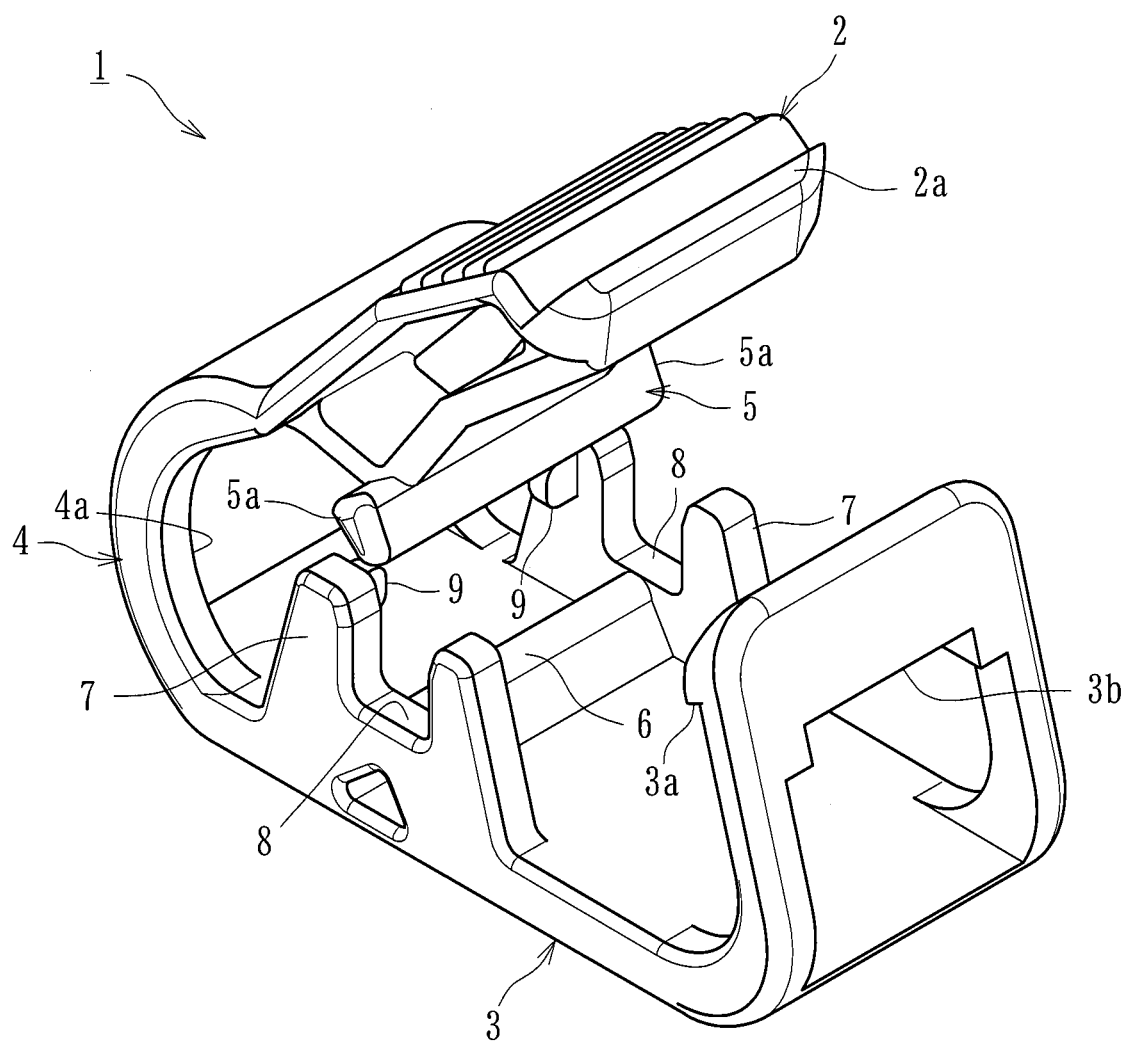
FIG. 1 A perspective view of a clamp device for a flexible tube of a first embodiment of the present invention.
Figure 2:
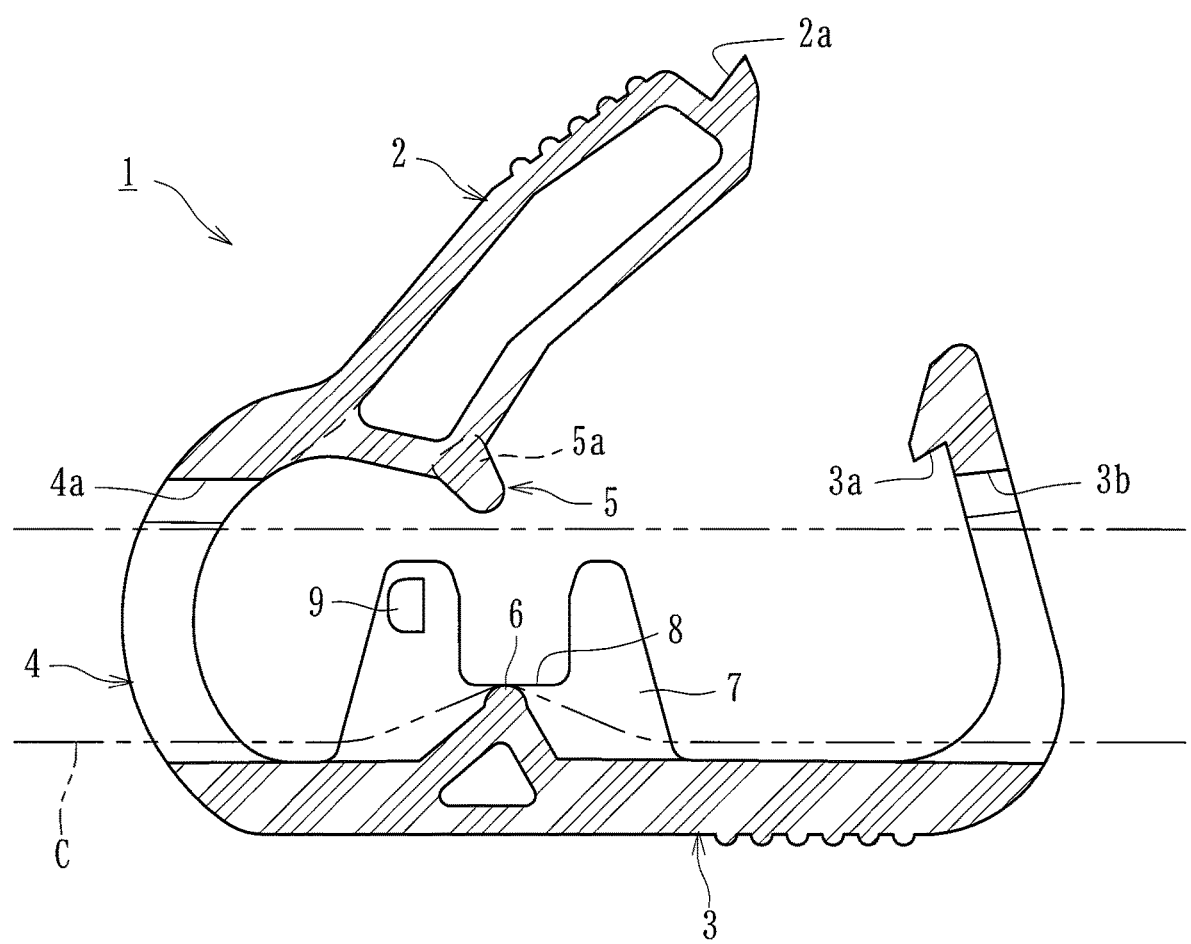
FIG. 2 A cross-section view of the clamp device for the flexible tube showing a state of the clamp device before clamping of the flexible tube.
Figure 3A:
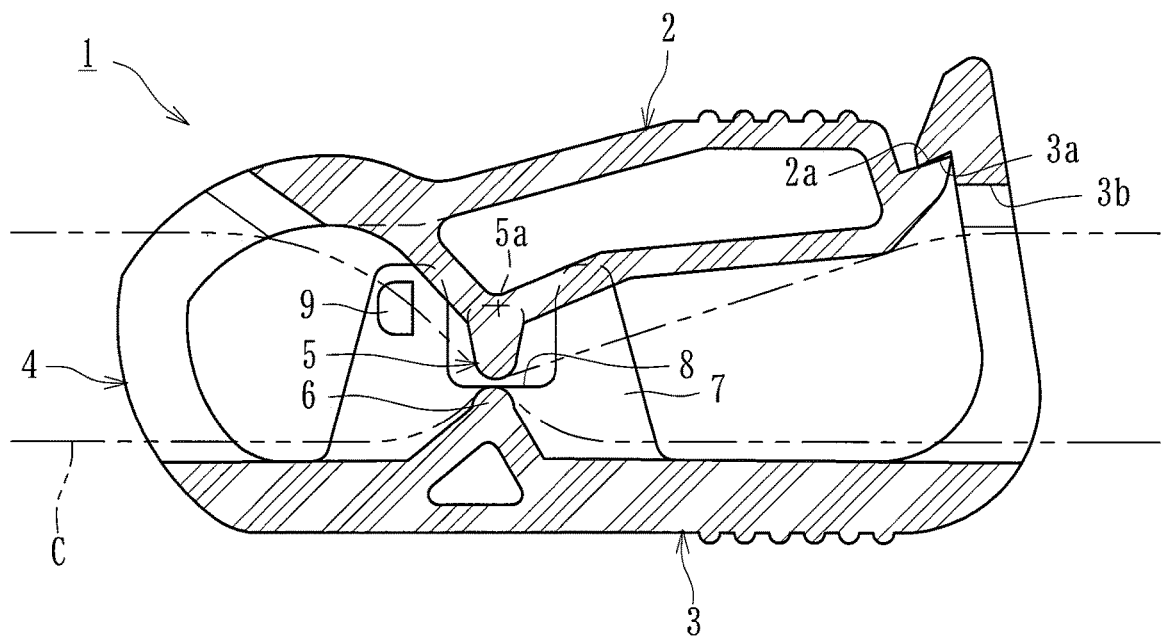
FIG. 3A A cross-section view showing a state of the clamp device after clamping of the flexible tube.
Figure 3B:
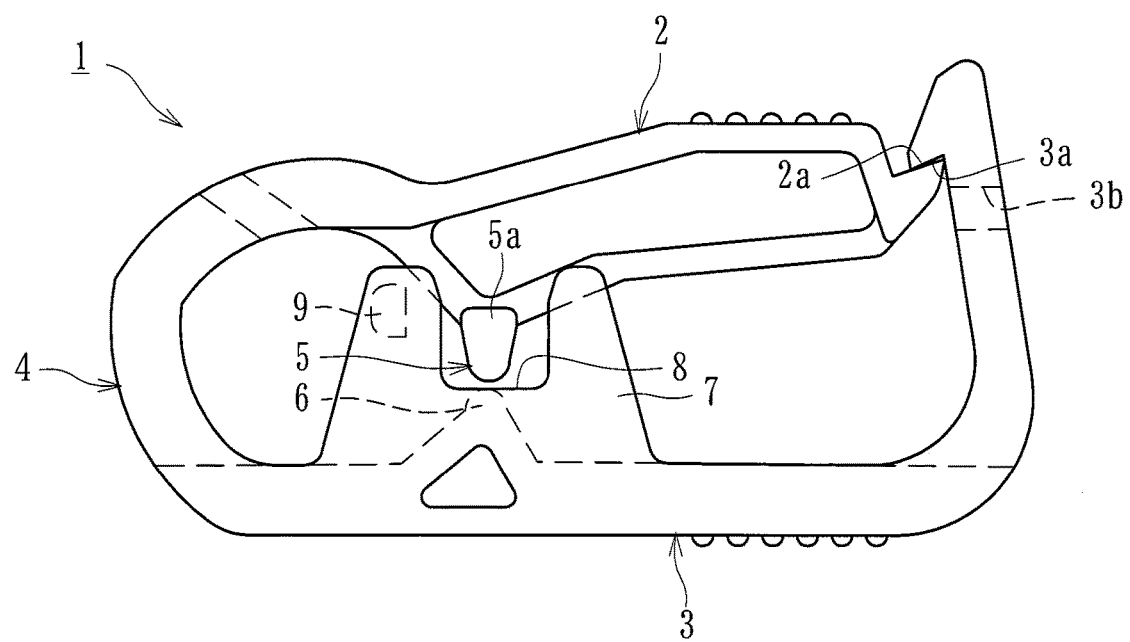
FIG. 3B A side-elevation view showing a state of the clamp device after clamping of the flexible tube (flexible tube being omitted)

A clamp device for a flexible tube of the first embodiment of the present invention can be used for clamping a flexible tube forming flow passages of a blood circuit of a dialysis apparatus or circuits for passing chemicals or physiological saline therethrough extending from various structural element of the blood circuit to block the flow of fluid and has a structure shown in FIGS. 1 to 3.

The clamp device 1 mainly comprises one branch 2 formed with a first projection 5, the other branch 3 formed with a second projection 6 opposing to the first projection 5, and an intermediate part 4 connecting the one branch 2 and the other branch 3 each other. These parts are integrally formed of predetermined resins (e.g. as polypropylene, olefin-based resin or polyethylene etc.). A state before clamping a flexible tube C is shown in FIGS. 1 and 2 and a state after clamping the flexible tube C is shown in FIG. 3.

An inner surface (lower surface in FIGS. 2 and 3) of the one branch 2 is formed with a first projection 5 downwardly extending from the inner surface of the one branch 2 and an outer surface (upper surface in FIGS. 2 and 3) is formed with knurls for preventing slippage of a finger of an operator during the clamping operation. In addition, a tip end of the one branch 2 is formed with an engaged part 2a, which is formed to have an acute angle as viewed from the thickness direction (view of FIG. 2), that enables smooth engagement with an engaging part 3a described below.

The intermediate part 4 is positioned between the one branch 2 and the other branch 3 and formed with a through aperture 4a for passing the flexible tube C therethrough. An operator can attain a clamped condition shown in FIG. 3 by bending the intermediate part 4 to move the tip end of the one branch 2 toward the tip end of the other branch 3 and engage the engaged part 2a of the one branch 2 with the engaging part 3a of the other branch 3.

As shown in FIGS. 2 and 3, the other branch 3 comprises a substantially horizontally extending base part and an upstanding part extending substantially vertically from the base part and the second projection 6 is formed on the substantially horizontally extending base part. The second projection 6 is formed at a position opposite to the first projection 5 and a space between the first and second projections 5, 6 before clamping of the flexible tube C is set so that the flexible tube C can be passed through the space between the first projection 5 and the second projection 6. In addition, the other through aperture 3b for passing the flexible tube C therethrough is also formed on the upstanding part of the other branch 3. Accordingly, it is possible to arrange the flexible tube C between the first and second projections 5, 6 by passing the flexible tube C through both the one through aperture 4a and the other through aperture 3b.

Furthermore, the engaging part 3a previously mentioned is formed on the tip end of the upstanding part of the other branch 3. More particularly, an inner surface of the tip end of the other branch 3 has a gently convex configuration enabling the engaged part 2a formed on the tip end of the one branch 2 to slide on the convex surface of the engaging part 3a. The inner surface of the tip end of the other branch 3 also has a step at a predetermined position to form the engaging part 3a. Once the engaged part 2a of the one branch 2 is engaged with the engaging part 3a of the other branch 3, it is possible to prevent the one branch 2 from being returned to the initial position by elastic spring force of the intermediate part 4 and thus possible to maintain the state shown in FIG. 3.

As described above, when the engaged part 2a of the one branch 2 is engaged with the engaging part 3a of the other branch 3 (see FIG. 3), the flexible tube C is sandwiched and pressed between the first and second projections 5, 6 and accordingly the flow of fluid within the flexible tube C can be blocked. That is, a portion of the flexible tube C passed through both the apertures 4a, 3b is strongly pressed by the first and second projections 5, 6 to close the flow passage of the flexible tube C.

According to the clamp device 1 of this embodiment of the present invention, a pair of wall parts 7 is formed on both sides of the base part of the other branch 3 substantially vertically extending toward the one branch 2 and a fitted part 8 comprising a concave part opened toward the one branch 2 is formed on each wall part 7. The fitted part 8 is located between two opposing projections of each wall part 7 and the two opposing projections are the same height. These fitted parts 8 can be fitted by fitting parts 5a formed on both ends of the first projection 5 under a state in which the flexible tube C is clamped with the engaged part 2a of the one branch 2 being engaged with the engaging part 3a of the other branch 3. The first projection 5 and the other branch being equal in width. That is, the relative positioning of the first projection 5 and the second projection 6 in the longitudinal direction of the flexible tube C can be achieved by fitting the fitting parts 5a into the fitted parts 8 under the state in which the engaged part 2a of the one branch 2 is engaged by the engaging part 3a of the other branch 3. As shown in FIGS. 1-3B the tip of the second projection and the concave part of the fitted part are coplanar.

Thus, the fitting parts 5a and the fitted parts 8 form "positioning part" of the present invention. The positioning part (i.e. fitting part 5a and fitted part 8) enables the first and second projections 5, 6 to be relatively positioned in the longitudinal direction of the flexible tube C (a direction orthogonally intersecting extension directions of the first and second projections 5, 6, i.e. a right and left direction in FIG. 3) under the clamped state of the flexible tube C with engaging the engaging part 3a and the engaged part 2a each other.

According to this embodiment of the present invention, since the clamp device 1 is provided with the positioning part (i.e. fitting part 5a and fitted part 8) which can perform the relative positioning of the first and second projections 5, 6 in the longitudinal position of the flexible tube C under the clamped state of the flexible tube C with engaging the engaging part 3a and the engaged part 2a each other, it is possible to minimize the sealing area with preventing the leakage of fluid during clamping operation and easily release the clamping of the flexible tube C. More particularly, since the positioning part of this embodiment comprises the fitting parts 5a and the fitted parts 8 formed respectively on the one branch 2 and the other branch 3 and the relative positioning of the first and second projections 5, 6 can be performed by fitting the fitting part 5a into the fitted part 8 under the state in which the engaging part 3a of the other branch 3 and the engaged part 2a of the one branch 2 are engaged each other, it is possible to more securely perform the relative positioning of the first and second projections 5, 6 in the longitudinal direction of the flexible tube C.

In addition, since the clamp device 1 comprises wall parts 7, 7 extending substantially vertically from both side edges of the other branch 3 and the fitted parts 8, 8 are formed on the wall parts 7, 7, it is possible to more smoothly and surely perform fitting of the fitting parts 5a, 5a into the fitted parts 8, 8. In this case, it may be possible to form the wall parts 7, 7 and the fitted parts 8, 8 on the one branch 2 and the fitting parts 5a, 5a on the other branch 3.

In addition, the pair of wall parts 7 of this embodiment extending substantially vertically from both side edges of the one branch 2 or the other branch 3 can also guide the one branch 2 during engagement of the engaged part 2a with the engaging part 3a. Thus, according to the clamp device 1 of this embodiment, the provision of the positioning part (i.e. the fitting part 5a and fitted part 8) and wall parts 7 enables the guidance of the one branch 2 in addition to the relative positioning of the first and second projections 5, 6 in the longitudinal direction of the flexible tube C.

Furthermore, the pair of wall parts 7 is formed with separator parts 9, 9 projected from inner surfaces of the wall parts 7 toward inside of the clamp device 1. The separator parts 9, 9 intend to separate the flexible tube C laid between the first projection 5 and the second projection 6 away from the wall parts 7. Thus, according to the clamp device of this embodiment, since it is provided with the positioning part (i.e. fitting part 5a and fitted part 8) and the separator parts 9, it is possible to perform a radial positioning of the flexible tube C in addition to the longitudinal positioning of the first and second projections 5, 6 in the longitudinal direction of the flexible tube C.

The engaging part 3*a* is formed on the tip end of the other branch 3 and adapted to be engaged by the engaged part 2*a* formed on the tip end of the one branch 2 and the first projection 5, the second projection 6 and the positioning part (fitting part 5*a* and fitted part 8 in this embodiment) are formed at positions nearer to the intermediate part 4 than formed positions of the engaged part 2*a* and the engaging part 3*a* respectively of the one branch 2 and the other branch 3. Accordingly, it is possible to perform the engagement of the engaging part 3*a* and the engaged part 2*a* with smaller force as well as to more securely perform the relative positioning of the first and second projections 5, 6 in the longitudinal direction of the flexible tube C.

Figure 13:
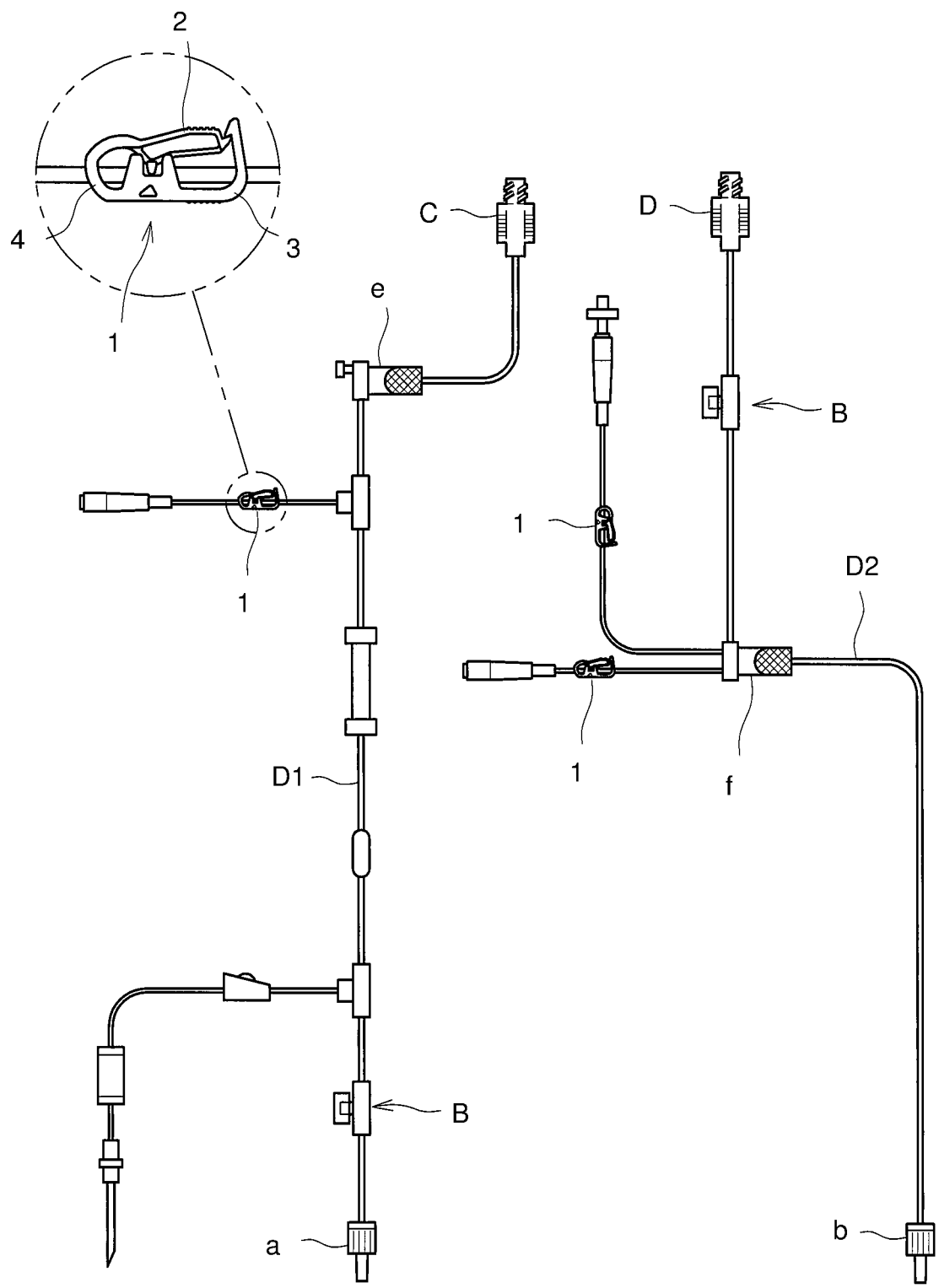
FIG. 13 A schematic view showing a medical instrument circuit to which the clamp device of the present invention is attached.

As shown in FIG. 13, the clamp device 1 of this embodiment can be used in a blood circuit (medical instrument circuit) having an arterial blood circuit D1 and venous blood circuit D2 for extracorporeally circulating blood of a patient (this is also applied to the clamp devices 1 of the second through fourth embodiments described below). That is, the clamp device is applied to any flow circuits or branch flow circuits of the arterial blood circuit D1 and venous blood circuit D2 to block extracorporeally circulating flow of blood or physiological saline. FIG. 13 shows that the clamp devices 1 are attached to a flow passage branched from the arterial blood circuit D1 and a flow passage extending from a venous air trap chamber "f" connected to the venous blood circuit D2. The clamp device may be applied to any position of the flexible tube used for the medical instrument circuit.

The arterial blood circuit D1 has at its tip end a shunt connector "a" to which an arterial puncture needle is attached, an arterial air trap chamber "e" connected at its middle, and a dialyzer connector "c" at its base end connectable to an arterial connector of a blood purification device (dialyzer). In addition, the venous blood circuit D2 has at its tip end a shunt connector "b" to which a venous puncture needle is attached, a venous air trap chamber "f" connected at its middle, and a dialyzer connector "d" at its base end connectable to a venous connector of a blood purification device (dialyzer). A character "B" denotes a rubber button (mixture injection member) which can inject medicines into the flexible tube or collect blood etc.

Then a second embodiment of the present invention will be described.

Figure 4:
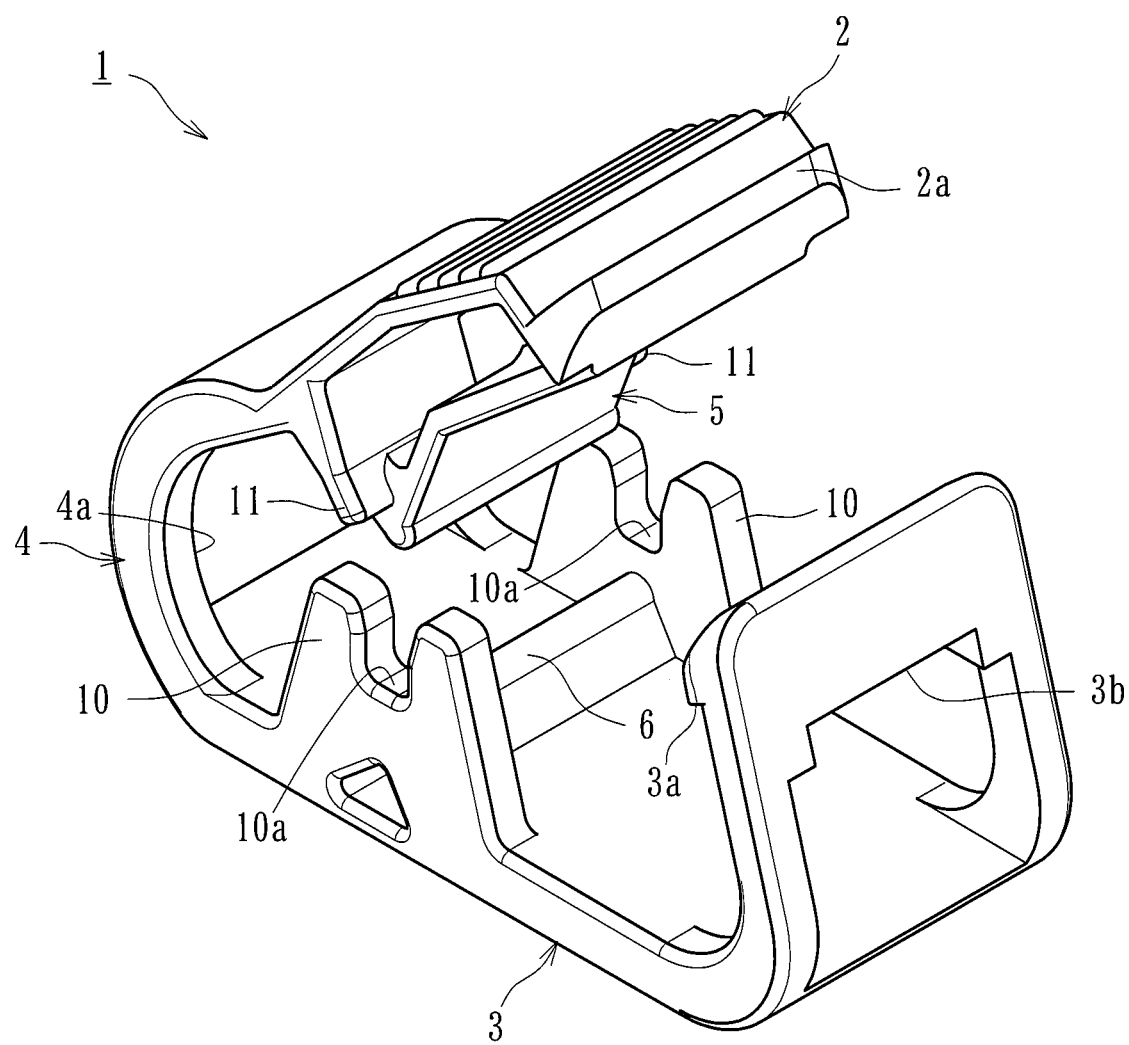
FIG. 4 A perspective view of a clamp device for a flexible tube of a second embodiment of the present invention.
Figure 5:
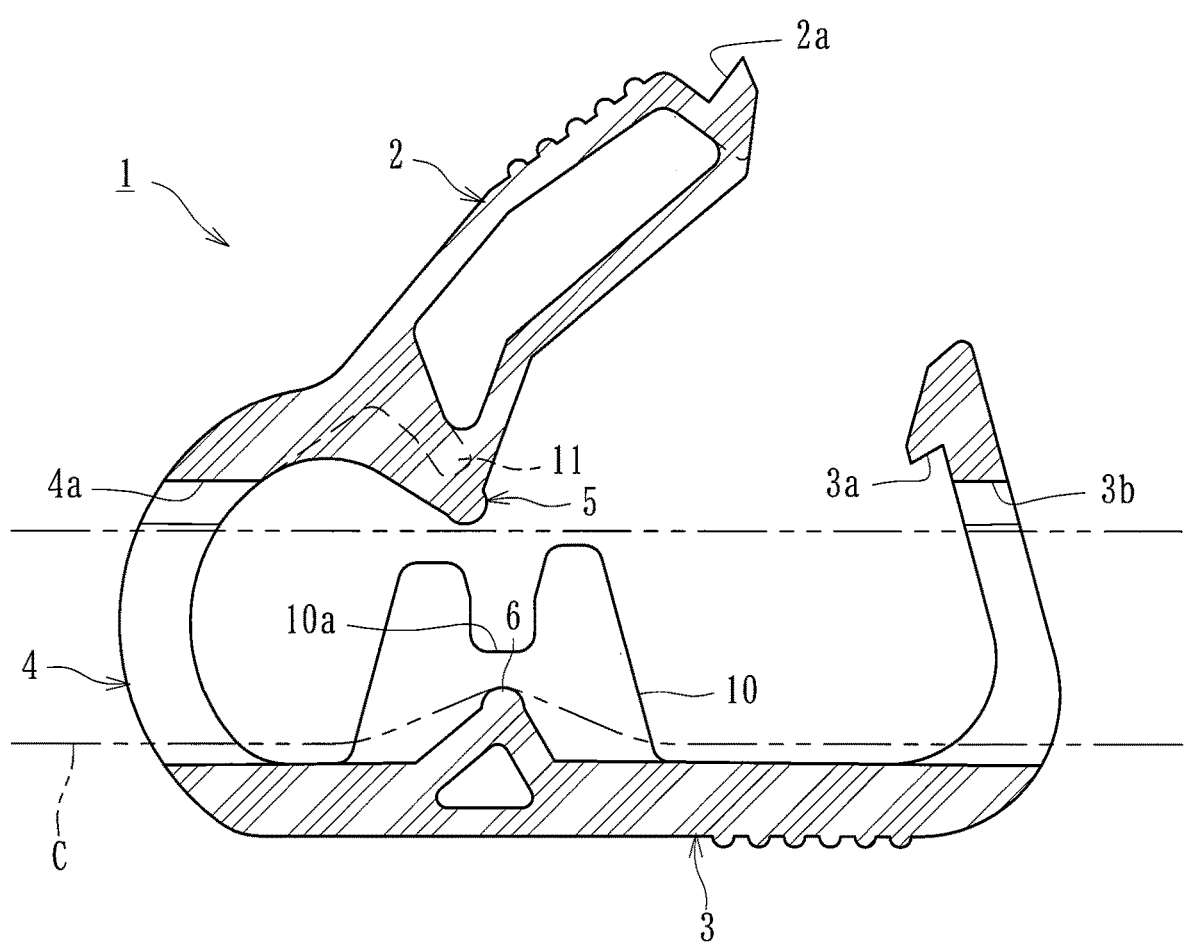
FIG. 5 A cross-section view of the clamp device for the flexible tube showing a state of the clamp device before clamping of the flexible tube.
Figure 6A:
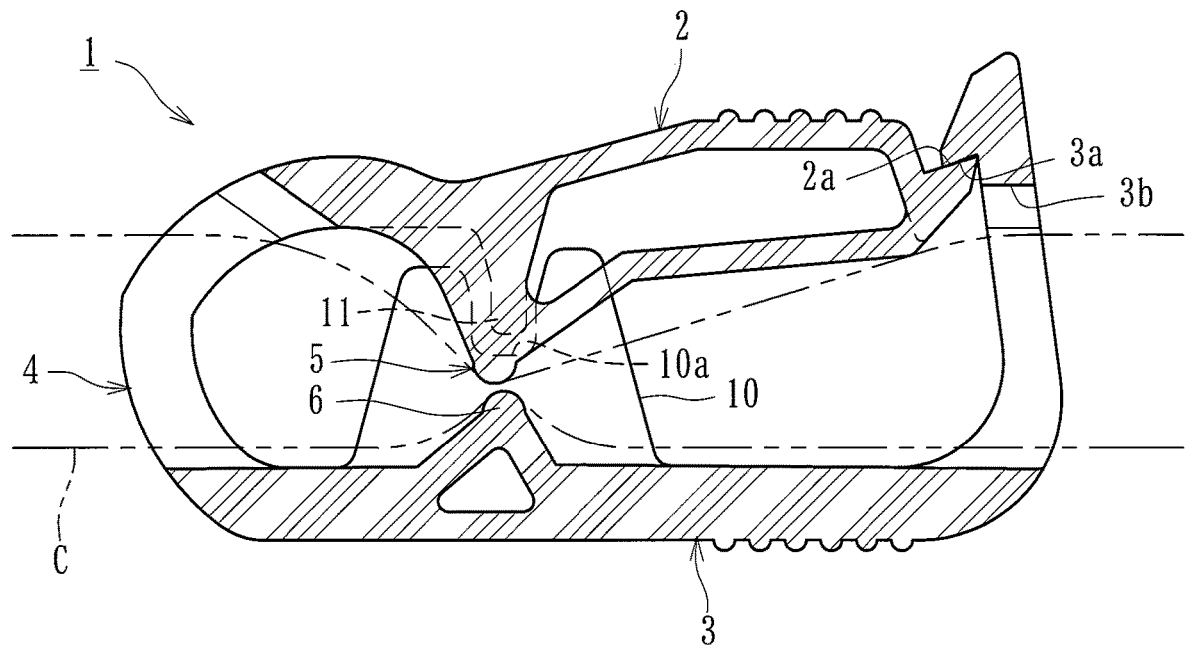
FIG. 6A A cross-section view showing a state of the clamp device after clamping of the flexible tube.
Figure 6B:
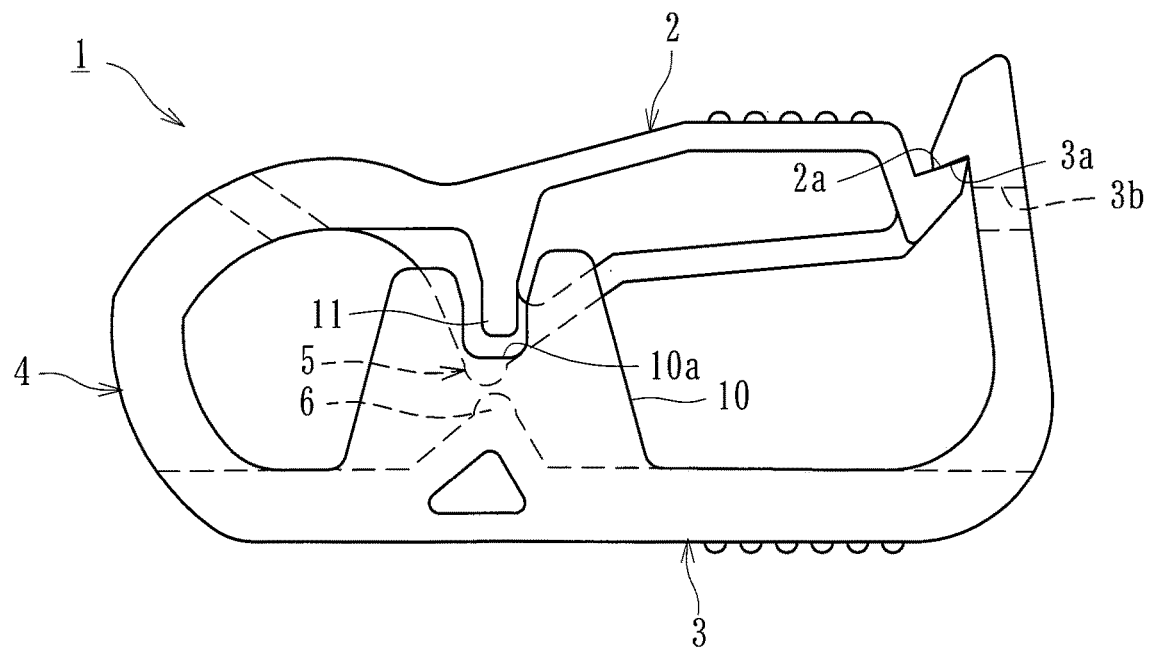
FIG. 6B A side-elevation view showing a state of the clamp device after clamping of the flexible tube (flexible tube being omitted)

Similarly to the first embodiment, the clamp device for a flexible tube of the second embodiment can be used for clamping a flexible tube forming flow passages of a blood circuit of a dialysis apparatus or circuits for passing chemicals or physiological saline extending from various structural element of the blood circuit to block the flow of fluid and has a structure shown in FIGS. 4 to 6. Same reference numerals are used in this embodiment as those used to parts of the first embodiment.

According to the clamp device 1 of this embodiment of the present invention, a pair of wall parts 10 is formed on both sides of the base part of the other branch 3 substantially vertically extending toward the one branch 2 and a concave part (fitted part) 10*a* opened toward the one branch 2 is formed on each wall part 10. As shown in FIG. 6, these concave parts 10*a* can be fitted by convex parts (fitting parts) 11 formed on both ends of the first projection 5 under a state in which the flexible tube C is clamped with the engaged part 2*a* of the one branch 2 being engaged with the engaging part 3*a* of the other branch 3. That is, the relative positioning of the first projection 5 and the second projection 6 in the longitudinal direction of the flexible tube C can be achieved by fitting the convex parts 11 into the concave parts 10*a* under the state in which the engaged part 2*a* of the one branch 2 is engaged by the engaging part 3*a* of the other branch 3.

Thus, the convex parts (fitting parts) 11 and the concave parts (fitted parts) 10*a* form "positioning part" of the present invention. The positioning part enables the first and second projections 5, 6 to be relatively positioned in the longitudinal direction of the flexible tube C (a direction orthogonally intersecting extension directions of the first and second projections 5, 6, i.e. a right and left direction in FIG. 6) under the clamped state of the flexible tube C with engaging the engaging part 3*a* and the engaged part 2*a* each other.

According to this embodiment of the present invention, since the clamp device 1 is provided with the positioning part (i.e. convex parts 11 and concave parts 10*a*) which can perform the relative positioning of the first and second projections 5, 6 in the longitudinal position of the flexible tube C under the clamped state of the flexible tube C with engaging the engaging part 3*a* and the engaged part 2*a* each other, it is possible to minimize the sealing area with preventing the leakage of fluid during clamping operation and easily release the clamping of the flexible tube C. More particularly, since the positioning part of this embodiment comprises the concave parts 10*a* formed on the other branch 3 and the convex parts 11 formed on the one branch 2 separately from the first projection 5 and the relative positioning of the first and second projections 5, 6 can be performed by fitting the convex parts 11 into the concave parts 10*a* under the state in which the engaging part 3*a* of the other branch 3 and the engaged part 2*a* of the one branch 2 are engaged each other, it is possible to more securely perform the relative positioning of the first and second projections 5, 6 in the longitudinal direction of the flexible tube C.

In addition, since the clamp device 1 comprises wall parts 10, 10 extending substantially vertically from both side edges of the other branch 3 and the concave parts 10*a*, 10*a* are formed on the wall parts 10, 10, it is possible to more smoothly and surely perform fitting of the convex portions 11, 11 into the concave portions 10*a*, 10*a*. In this case, it may be possible to form the wall parts 10, 10 formed with the concave parts 10*a*, 10*a* on the one branch 2 and the convex parts 11, 11 on the other branch 3.

In addition, the pair of wall parts 10 of this embodiment extends substantially vertically from both side edges of the one branch 2 or the other branch 3 and is able to guide the one branch 2 during engagement of the engaged part 2*a* with the engaging part 3*a*. Thus, according to the clamp device 1 of this embodiment, the provision of the positioning part (i.e. convex parts 11 and concave parts 10*a*) and wall parts 10 enables the guidance of the one branch 2 in addition to the relative positioning of the first and second projections 5, 6 in the longitudinal direction of the flexible tube C.

The engaging part 3*a* is formed on the tip end of the other branch 3 and adapted to be engaged by the engaged part 2*a* formed on the tip end of the one branch 2 and the first projection 5, the second projection 6 and the positioning part (convex parts 11 and concave parts 10*a* in this embodiment) are formed at positions nearer to the intermediate part 4 than the formed positions of the engaged part 2*a* and the engaging part 3*a* respectively of the one branch 2 and the other branch 3. Accordingly, it is possible to perform the engagement of the engaging part 3*a* and the engaged part 2*a* with smaller force as well as to more securely perform the relative positioning of the first and second projections 5, 6 in the longitudinal direction of the flexible tube C.

Then a third embodiment of the present invention will be described.

Figure 7:
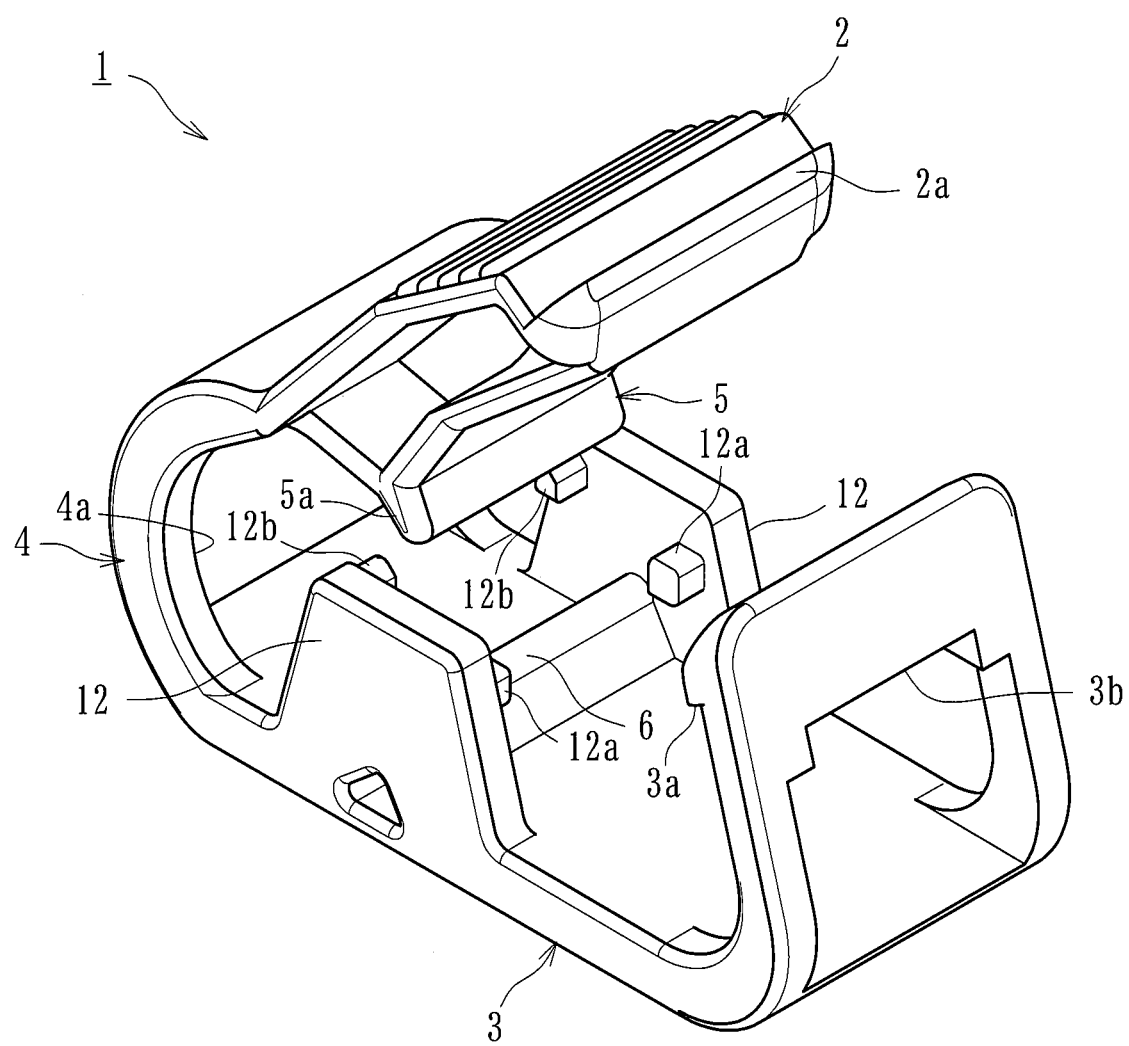
FIG. 7 A perspective view of a clamp device for a flexible tube of a third embodiment of the present invention.
Figure 8:
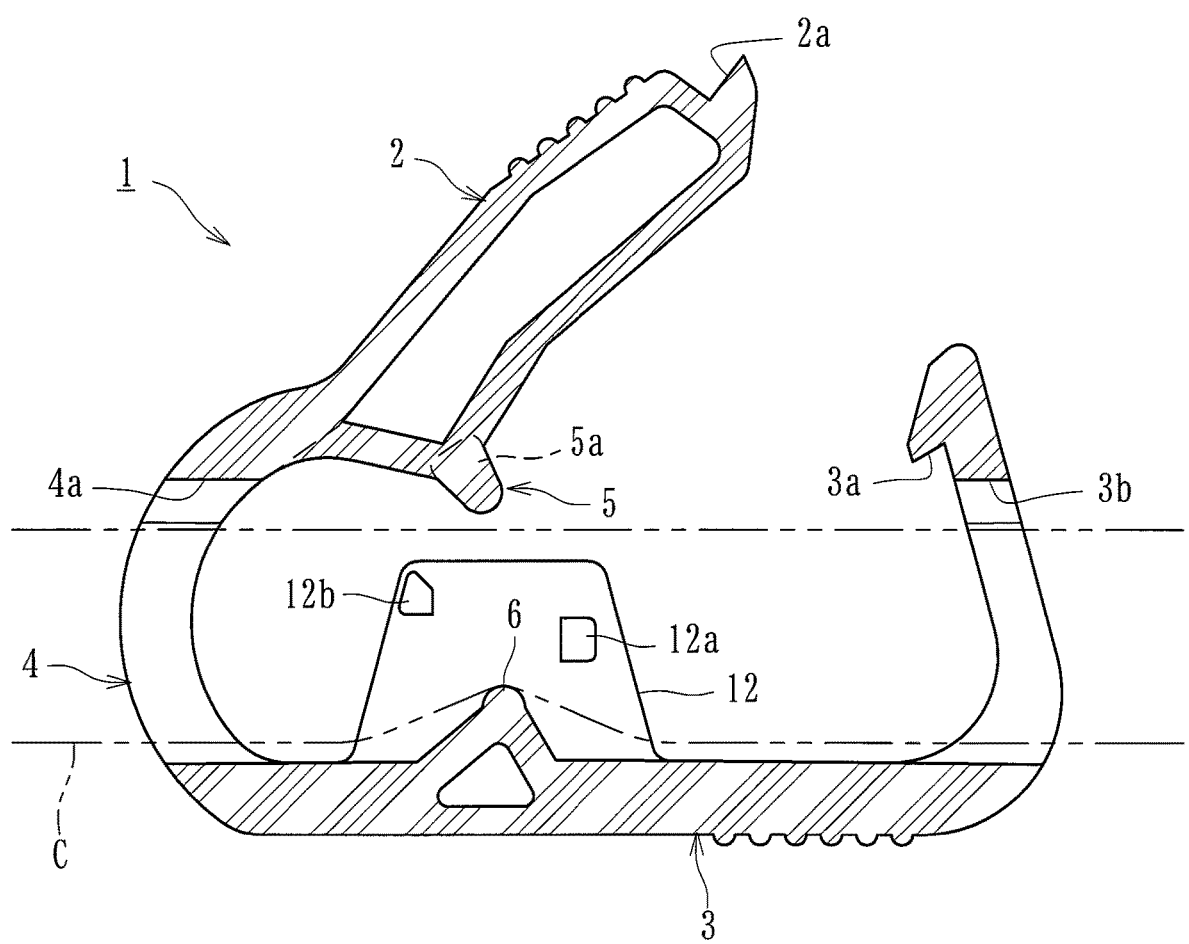
FIG. 8 A cross-section view of the clamp device for the flexible tube showing a state of the clamp device before clamping of the flexible tube.
Figure 9A:
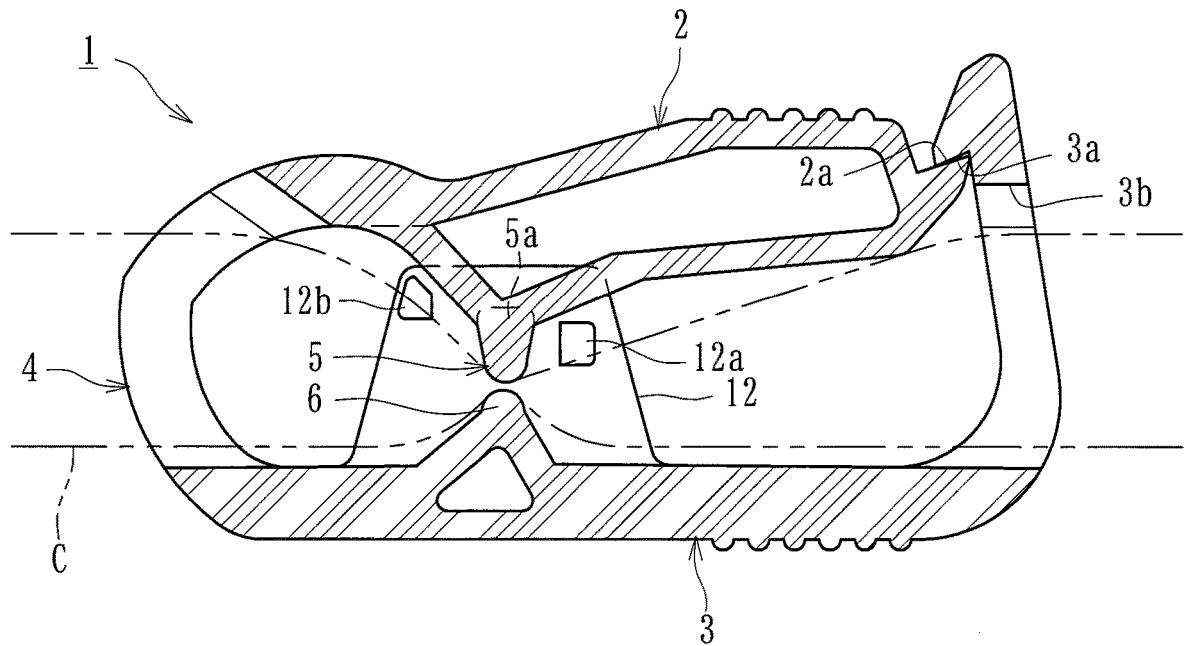
FIG. 9A A cross-section view showing a state of the clamp device after clamping of the flexible tube.
Figure 9B:
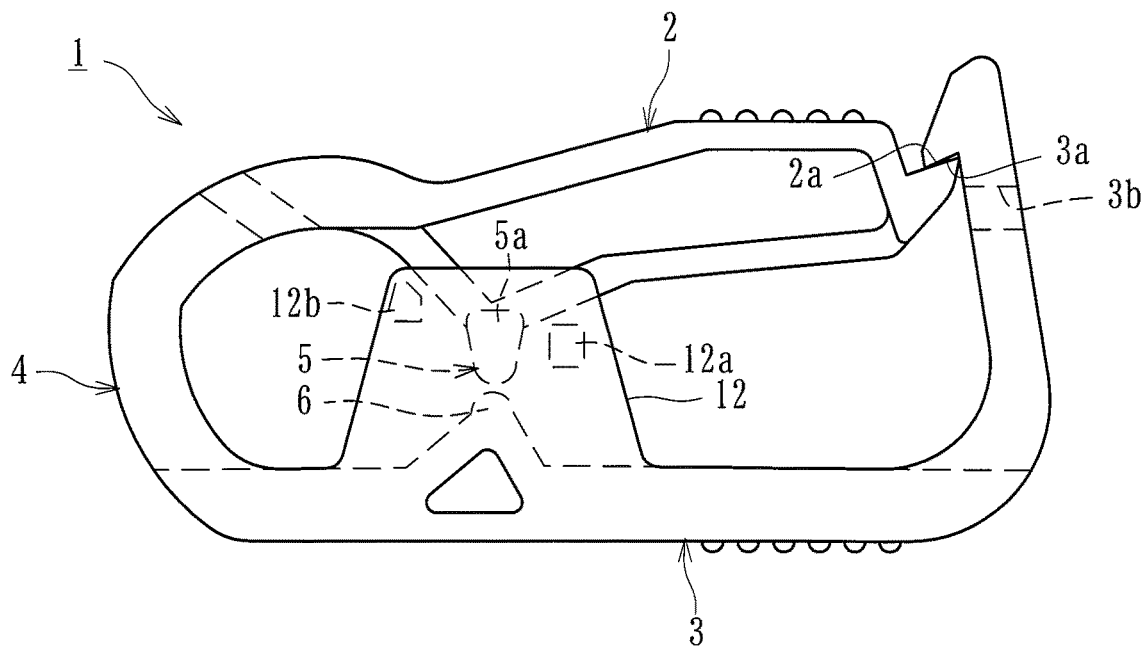
FIG. 9B A side-elevation view showing a state of the clamp device after clamping of the flexible tube (flexible tube being omitted)

Similarly to the previous embodiments, the clamp device for a flexible tube of the third embodiment can be used for clamping a flexible tube forming flow passages of a blood circuit of a dialysis apparatus or circuits for passing chemicals or physiological saline therethrough extending from various structural element of the blood circuit to block the flow of fluid and has a structure shown in FIGS. 7 to 9. Same reference numerals are used also in this embodiment as those used to parts of the previous embodiments.

According to the clamp device 1 of this embodiment of the present invention, a pair of wall parts 12 is formed on both sides of the base part of the other branch 3 substantially vertically extending toward the one branch 2 and a pair of protruding parts (fitted parts) 12a, 12b is formed on each inner surface (opposing surface) of the wall part 12. As shown in FIG. 9, these protruding parts 12a, 12b are separated a predetermined space each other and fitting parts 5a comprising both ends of the first projection 5 can be fitted into the space between the pair of protruding parts 12a, 12b under a state in which the flexible tube C is clamped with the engaged part 2a of the one branch 2 being engaged with the engaging part 3a of the other branch 3. That is, the relative positioning of the first projection 5 and the second projection 6 in the longitudinal direction of the flexible tube C can be achieved by fitting the fitting parts 5a into the space between the protruding parts 12a, 12b under the state in which the engaged part 2a of the one branch 2 is engaged by the engaging part 3a of the other branch 3.

Thus, the protrusion parts (fitted parts) 12a, 12b and the fitting parts (fitting parts) 5a form "positioning part" of the present invention. The positioning part enables the first and second projections 5, 6 to be relatively positioned in the longitudinal direction of the flexible tube C (a direction orthogonally intersecting extension directions of the first and second projections 5, 6, i.e. a right and left direction in FIG. 9) under the clamped state of the flexible tube C with engaging the engaging part 3a and the engaged part 2a each other.

According to this embodiment of the present invention, since the clamp device 1 is provided with the positioning part (i.e. protrusion parts (fitted parts) 12a, 12b and the fitting parts (fitting parts) 5a) which can perform the relative positioning of the first and second projections 5, 6 in the longitudinal position of the flexible tube C under the clamped state of the flexible tube C with engaging the engaging part 3a and the engaged part 2a each other, it is possible to minimize the sealing area with preventing the leakage of fluid during clamping operation and easily release the clamping of the flexible tube C. More particularly, since the positioning part of this embodiment comprises the protrusion parts 12a, 12b formed on the one branch 2 and the fitting parts 5a formed on the other branch 3 and the relative positioning of the first and second projections 5, 6 can be performed by fitting the fitting parts 5a into the space between the protrusion parts 12a, 12b under the state in which the engaging part 3a of the other branch 3 and the engaged part 2a of the one branch 2 are engaged each other, it is possible to more securely perform the relative positioning of the first and second projections 5, 6 in the longitudinal direction of the flexible tube C.

In addition, since the clamp device 1 comprises wall parts 12, 12 extending substantially vertically from both side edges of the other branch 3 and the protrusion parts 12a, 12b are formed on the wall parts 12, 12, it is possible to more smoothly and surely perform fitting of the protrusion parts 12a, 12b into the space between the protrusion parts 12a, 12b. In this case, it may be possible to form the wall parts 12, 12 having the protrusion parts 12a, 12b on the one branch 2 and the fitting parts 5a on the other branch 3.

Furthermore, the pair of wall parts 12 of this embodiment extends substantially vertically from both side edges of the one branch 2 or the other branch 3 and is able to guide the one branch 2 during engagement of the engaged part 2a with the engaging part 3a. Thus, according to the clamp device 1 of this embodiment, the provision of the positioning part (i.e. protrusion parts 12a, 12b and the fitting parts 5a) and wall parts 12 enables the guidance of the one branch 2 in addition to the relative positioning of the first and second projections 5, 6 in the longitudinal direction of the flexible tube C.

In addition, the protrusion parts 12a, 12b formed on the pair of wall parts 12 of this embodiment may have a function of radially separating the flexible tube C laid between the first and second projections 5, 6 similarly to the separator parts 9, 9 of the first embodiment. In this case, the protrusion parts 12a, 12b makes it possible to perform a radial positioning of the flexible tube C in addition to the longitudinal positioning of the first and second projections 5, 6 in the longitudinal direction of the flexible tube C.

The engaging part 3a is formed on the tip end of the other branch 3 and adapted to be engaged by the engaged part 2a formed on the tip end of the one branch 2 and the first projection 5, the second projection 6 and the positioning part (protrusion parts 12a, 12b and fitting parts 5a in this embodiment) are formed at positions nearer to the intermediate part 4 than the formed positions of the engaged part 2a and the engaging part 3a respectively of the one branch 2 and the other branch 3. Accordingly, it is possible to perform the engagement of the engaging part 3a and the engaged part 2a with smaller force as well as to more securely perform the relative positioning of the first and second projections 5, 6 in the longitudinal direction of the flexible tube C.

Then a fourth embodiment of the present invention will be described.

Figure 10:
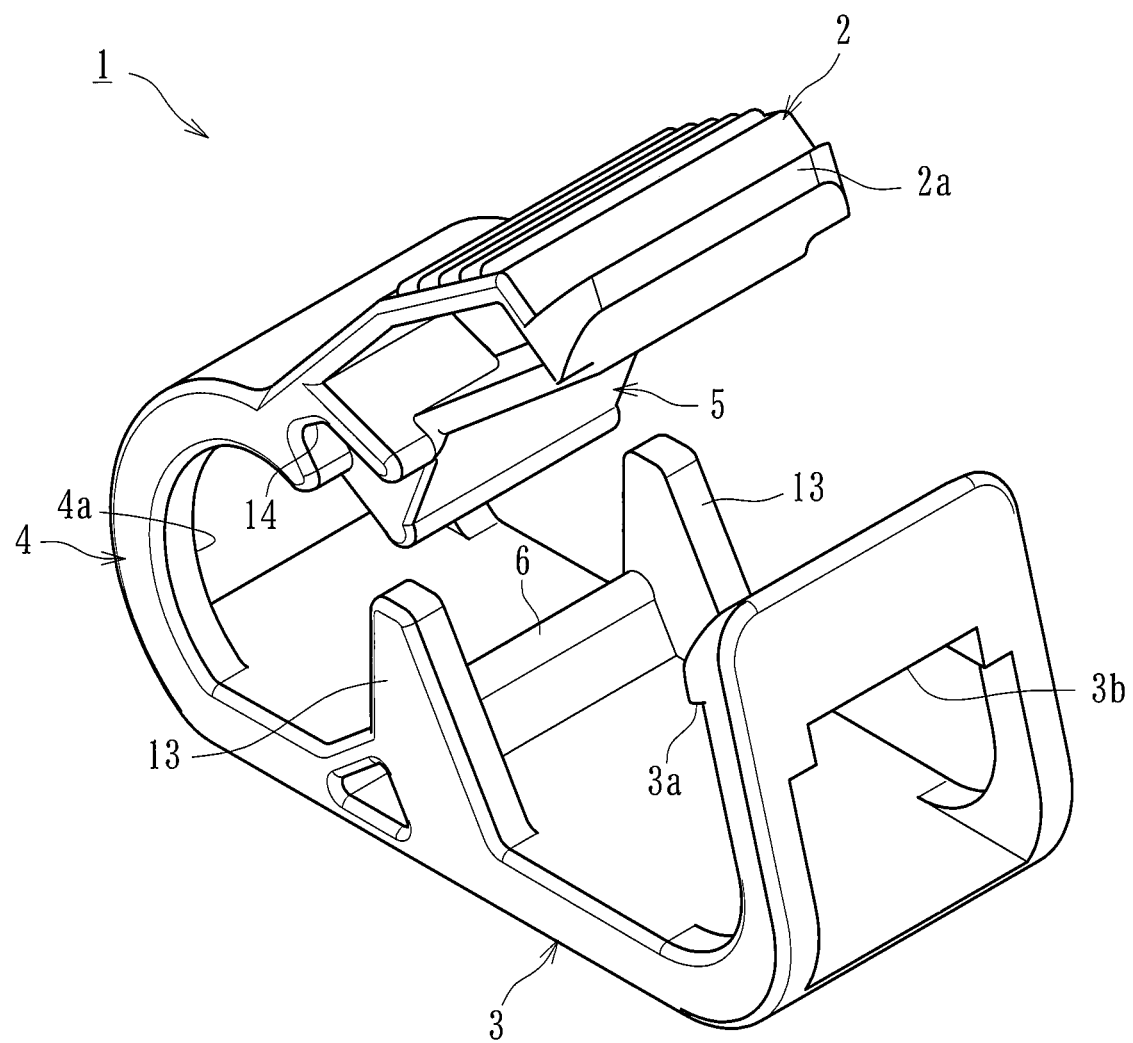
FIG. 10 A perspective view of a clamp device for a flexible tube of a fourth embodiment of the present invention.
Figure 11:
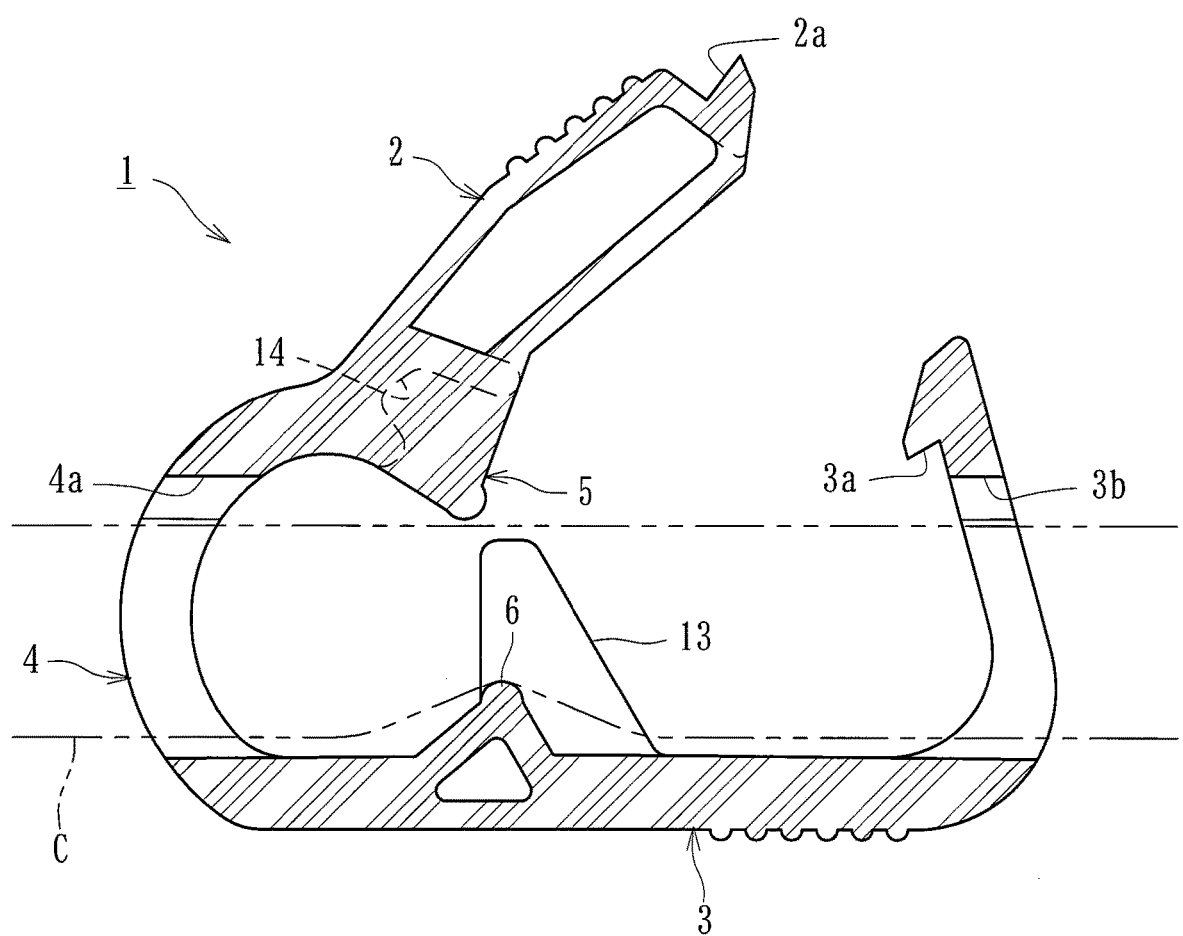
FIG. 11 A cross-section view of the clamp device for the flexible tube showing a state of the clamp device before clamping of the flexible tube.
Figure 12A:
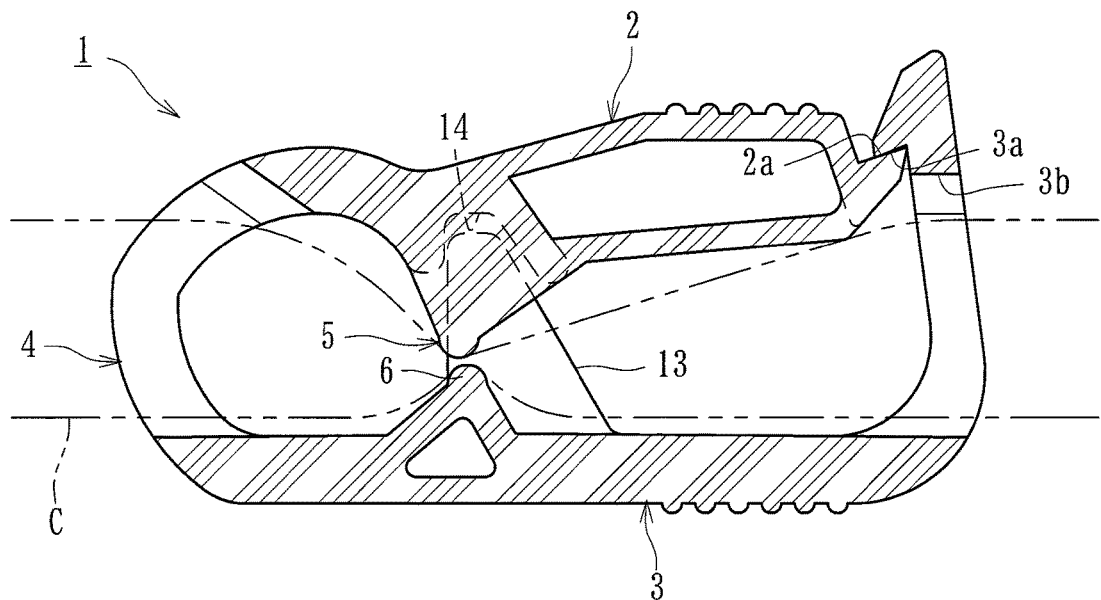
FIG. 12A A cross-section view showing a state of the clamp device after clamping of the flexible tube.
Figure 12B:
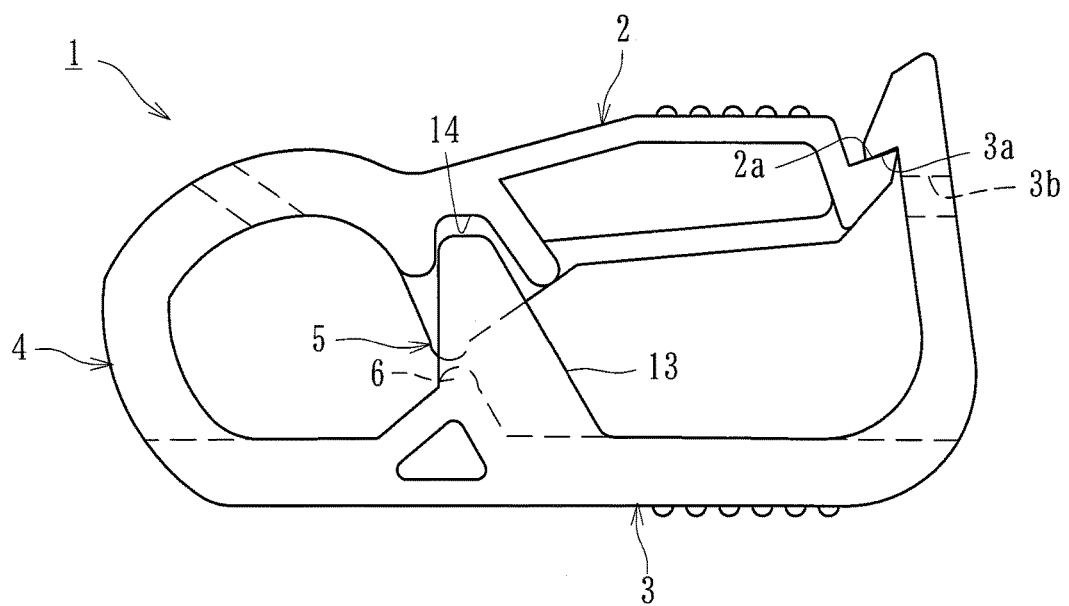
FIG. 12B A side-elevation view showing a state of the clamp device after clamping of the flexible tube (flexible tube being omitted)

Similarly to the previous embodiments, the clamp device for a flexible tube of the fourth embodiment can be used for clamping a flexible tube forming flow passages of a blood circuit of a dialysis apparatus or circuits for passing chemicals or physiological saline extending from various structural element of the blood circuit to block the flow of fluid and has a structure shown in FIGS. 10 to 12. Same reference numerals are used also in this embodiment as those used to parts of the previous embodiments.

According to the clamp device 1 of this embodiment of the present invention, a pair of convex parts (fitting parts) 13 is formed on both sides of the base part of the other branch 3 substantially vertically extending toward the one branch 2. These convex parts 13 can be fitted into a pair of concave grooves (fitted parts) 14 formed on the one branch 2 as shown in FIG. 12. That is, the relative positioning of the first projection 5 and the second projection 6 in the longitudinal direction of the flexible tube C can be achieved by fitting the convex parts 13 into the concave grooves 14 under the state in which the engaged part 2a of the one branch 2 is engaged by the engaging part 3a of the other branch 3.

Thus, the convex parts (fitting parts) 13 and the concave grooves (fitted parts) 14 form "positioning part" of the present invention. The positioning part enables the first and second projections 5, 6 to be relatively positioned in the longitudinal direction of the flexible tube C (a direction orthogonally intersecting extension directions of the first and second projections 5, 6, i.e. a right and left direction in FIG. 12) under the clamped state of the flexible tube C with engaging the engaging part 3a and the engaged part 2a each other.

According to this embodiment of the present invention, since the clamp device 1 is provided with the positioning part (i.e. the convex parts 13 and the concave grooves 14) which can perform the relative positioning of the first and second projections 5, 6 in the longitudinal position of the flexible tube C under the clamped state of the flexible tube C with engaging the engaging part 3a and the engaged part 2a each other, it is possible to minimize the sealing area with preventing the leakage of fluid during clamping operation and easily release the clamping of the flexible tube C. More particularly, since the positioning part of this embodiment comprises the concave grooves 14 formed on the one branch 2 and the convex parts 13 formed on the other branch 3 separate from the first and second projections 5, 6 and the relative positioning of the first and second projections 5, 6 can be performed by fitting the convex parts 13 into the concave grooves 14 under the state in which the engaging part 3a of the other branch 3 and the engaged part 2a of the one branch 2 are engaged each other, it is possible to more securely perform the relative positioning of the first and second projections 5, 6 in the longitudinal direction of the flexible tube C.

In addition, the pair of convex portions 13 may be formed so that they extend substantially vertically from both side edges of the one branch 2 or the other branch 3 to guide the one branch 2 during engagement of the engaged part 2a with the engaging part 3a. In this case, it is possible to perform guidance of the one branch 2 in addition to the relative positioning of the first and second projections 5, 6 in the longitudinal direction of the flexible tube C.

The engaging part 3a is formed on the tip end of the other branch 3 and adapted to be engaged by the engaged part 2a formed on the tip end of the one branch 2 and the first projection 5, the second projection 6 and the positioning part (convex parts 13 and concave grooves 14) are formed at positions nearer to the intermediate part 4 than the formed positions of the engaged part 2a and the engaging part 3a respectively of the one branch 2 and the other branch 3. Accordingly, it is possible to perform the engagement of the engaging part 3a and the engaged part 2a with smaller force as well as to more securely perform the relative positioning of the first and second projections 5, 6 in the longitudinal direction of the flexible tube C.

Although it has been described several embodiments of the present invention, the present invention is not limited to these embodiments and accordingly it may be possible to adopt a structure different from that for fitting the fitting part into the fitted parts as the relative positioning part of the first and second projections in the longitudinal direction of the flexible tube. Although it has illustrated and described the positioning parts of the first through fourth embodiments integrated to the clamp device 1, it may be possible to adhere or weld separately manufactured positioning parts to clamp devices.

The present invention can be applied to any clamp device for a flexible tube which can perform the relative positioning of the first and second projections in the longitudinal position of the flexible tube under the clamped state of the flexible tube with engaging the engaging part and the one branch each other.

REFERENCE NUMERALS 1 clamp device
2 one branch
3 the other branch
4 intermediate part
5 first projection
6 second projection
7 wall part
8 fitted part
9 separator part
10 wall part
10a concave groove (fitted part)
11 convex part (fitting part)
12 wall part
12a, 12b fitted part
13 convex part
14 concave groove (fitted part)
C flexible tube

What is claimed is:

1. A clamp device for a flexible tube comprising:
one branch formed with a first projection;
an other branch formed with a second projection opposing the first projection;
an elastically bendable intermediate part positioned between the one branch and the other branch and connecting the one branch and the other branch to each other;
an engaging part formed on the other branch adapted to be engaged with the one branch; wherein flow of fluid within the flexible tube laid between the first projection and the second projection is blockable by elastically bending the elastically bendable intermediate part and engaging the engaging part and the one branch with each other to clamp the flexible tube laid between the first projection and the second projection;
a positioning part for performing a relative positioning of the first and second projections in a longitudinal direction of the flexible tube under a clamped state of the flexible tube with the engaging part and the one branch engaging each other;
wherein the positioning part comprises:
a fitting part extending in an external direction from both ends of the first projection, and
a fitted part,
wherein the fitting part is formed on the one branch and the fitted part is formed on the other branch, and the fitting part comprises a convex part and the fitted part comprises a concave part, and wherein the relative positioning of the first projection and the second projection is achievable by fitting the convex part into the concave part under a state in which the one branch is engaged by the engaging part of the other branch; and
a pair of wall parts extending substantially vertically from both side edges of the other branch, and wherein the fitted parts are formed between each the pair of wall parts;
wherein the pair of wall parts enable the one branch to be guided during engagement of the one branch by the engaging part of the other branch;
wherein the engaging part is formed on a tip end of the other branch and adapted to be engaged by an engaged part formed on a tip end of the one branch, and wherein the first projection, the second projection, and the positioning part are formed at positions nearer to the elastically bendable intermediate part than formed positions of the engaged part and the engaging part respectively of the one branch and the other branch;
wherein the clamp device is configured for releasable clamping of the flexible tube.

2. The clamp device for a flexible tube of claim 1, wherein the clamp device further comprises separator parts projected from inner surfaces of the pair of wall parts toward an inside of the clamp device so that when the flexible tube is laid between the first projection and the second projection the flexible tube is separated away from the pair of wall parts.

3. The clamp device of claim 2, wherein the separator parts radially position the flexible tube and the positioning part longitudinally positions the flexible tube.

4. The clamp device of claim 2, wherein the separator parts are a pair of separator parts located on the pair of wall parts so that the pair of separator parts directly oppose one another.

5. The clamp device of claim 2, wherein the separator parts are positioned between the second projection and the elastically bendable intermediate part relative to a longitudinal axis of the clamp device.

6. The clamp device of claim 2, wherein, in an unclamped state, a height of the separator parts is positioned between a height of the first projection and a height of the second projection.

7. A medical instrument circuit to which the clamp device for the flexible tube of claim 1 is attached.

8. The clamp device of claim 1, wherein the engaged part is formed by a step located at the tip end of the one branch.

9. The clamp device of claim 1, wherein the clamp device is releasable and after being released is free of inelastic deformation or damage to the clamp device.

10. The clamp device of claim 1, wherein the fitted part is formed between two opposing projections of each of the pair of wall parts and the two opposing projections are a same height.

11. The clamp device of claim 1, wherein a tip of the second projection is coplanar with the concave part of the fitted part.

12. The clamp device of claim 1, wherein the fitted part is formed above the side edges of the one branch or the other branch.

13. The clamp device of claim 1, wherein a width of the first projection is equal to a width of the other branch.

14. The clamp device of claim 1, wherein the one branch and the other branch each include a plurality of knurls along an outer surface.

15. A clamp device for a flexible tube comprising:
one branch formed with a first projection;
an other branch formed with a second projection opposing the first projection;
an elastically bendable intermediate part positioned between the one branch and the other branch and connecting the one branch and the other branch to each other;
an engaging part formed on the other branch adapted to be engaged with the one branch; wherein flow of fluid within the flexible tube laid between the first projection and the second projection is blockable by elastically bending the elastically bendable intermediate part and engaging the engaging part and the one branch with each other to clamp the flexible tube laid between the first projection and the second projection;
a positioning part for performing a relative positioning of the first and second projections in a longitudinal direction of the flexible tube under a clamped state of the flexible tube with the engaging part and the one branch engaging each other;
wherein the positioning part comprises:
a fitting part, and
a fitted part,
wherein the fitting part is formed on the one branch and the fitted part is formed on the other branch, and the fitting part comprises a convex part and the fitted part comprises a concave part, and wherein the relative positioning of the first projection and the second projection is achievable by fitting the convex part into the concave part under a state in which the one branch is engaged by the engaging part of the other branch; and
wall parts extending substantially vertically from both side edges of the one branch or the other branch, and wherein the fitted part is formed on the wall parts;
wherein the wall parts enable the one branch to be guided during engagement of the one branch by the engaging part of the other branch;
wherein the engaging part is formed on a tip end of the other branch and adapted to be engaged by an engaged part formed on a tip end of the one branch, and wherein the first projection, the second projection, and the positioning part are formed at positions nearer to the elastically bendable intermediate part than formed positions of the engaged part and the engaging part respectively of the one branch and the other branch;
wherein the clamp device is configured for releasable clamping of the flexible tube; and wherein the concave part of the fitted part is positioned above a height of the second projection.

16. The clamp device for a flexible tube of claim 15, wherein the clamp device further comprises separator parts projected from inner surfaces of the wall parts toward an inside of the clamp device so that when the flexible tube is laid between the first projection and the second projection the flexible tube is separated away from the wall parts, and the separator parts radially position the flexible tube and the positioning part longitudinally positions the flexible tube.

17. The clamp device of claim 15, wherein the fitted part is formed above the side edges of the one branch or the other branch, and a width of the first projection is equal to a width of the other branch.

18. The clamp device of claim 15, wherein the fitting part extends from opposing ends of the first projection.

19. The clamp device of claim 15, wherein the separator parts are positioned between the second projection and the elastically bendable intermediate part relative to a longitudinal axis of the clamp device.

* * * * *